United States Patent
Inoo et al.

(10) Patent No.: US 10,149,834 B2
(45) Date of Patent: *Dec. 11, 2018

(54) ROPINIROLE-CONTAINING ADHESIVE PATCH

(71) Applicant: Teikoku Seiyaku Co., Ltd., Higashikagawa-shi, Kagawa (JP)

(72) Inventors: Katsuyuki Inoo, Higashikagawa (JP); Akiko Katayama, Higashikagawa (JP); Daiki Takano, Higashikagawa (JP)

(73) Assignee: Teikoku Seiyaku Co., Ltd., Higashikagawa-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/584,809

(22) Filed: May 2, 2017

(65) Prior Publication Data

US 2017/0231959 A1 Aug. 17, 2017
US 2018/0104217 A9 Apr. 19, 2018

Related U.S. Application Data

(63) Continuation of application No. 14/362,001, filed as application No. PCT/JP2012/081083 on Nov. 30, 2012, now Pat. No. 9,849,095.

(60) Provisional application No. 61/565,850, filed on Dec. 1, 2011.

(51) Int. Cl.
| | |
|---|---|
| *A61K 31/58* | (2006.01) |
| *A61K 31/56* | (2006.01) |
| *A61K 31/353* | (2006.01) |
| *A61K 31/4166* | (2006.01) |
| *A61K 31/473* | (2006.01) |
| *A61K 31/407* | (2006.01) |
| *G01N 33/50* | (2006.01) |
| *C12Q 1/68* | (2018.01) |
| *A61K 31/4045* | (2006.01) |
| *A61K 9/70* | (2006.01) |

(52) U.S. Cl.
CPC ........ *A61K 31/4045* (2013.01); *A61K 9/7061* (2013.01)

(58) Field of Classification Search
None
See application file for complete search history.

(56) References Cited

U.S. PATENT DOCUMENTS

| | | | |
|---|---|---|---|
| 5,783,208 A | 7/1998 | Venkateshwaran et al. | |
| 5,807,570 A | 9/1998 | Chen et al. | |
| 2004/0247656 A1* | 12/2004 | Beier | A61K 9/7061 |
| | | | 424/449 |
| 2011/0195109 A1 | 8/2011 | Michinaka et al. | |

FOREIGN PATENT DOCUMENTS

| | | |
|---|---|---|
| EP | 2 255 802 A1 | 2/2009 |
| JP | H11-506462 A | 6/1999 |
| JP | 2001-518058 A | 10/2001 |
| JP | 2011-51986 A | 3/2011 |
| JP | 2000-514695 A | 11/2012 |
| WO | WO 96/39136 | 12/1996 |
| WO | WO 97/11696 | 4/1997 |
| WO | WO 2007/031265 A2 | 3/2007 |
| WO | WO 2009/107478 A1 | 9/2009 |

OTHER PUBLICATIONS

International Search Report dated Dec. 25, 2012 with English translation (five (5) pages).
Japanese-language Written Opinion (PCT/ISA/237) dated Dec. 25, 2012 (four (4) pages).

* cited by examiner

*Primary Examiner* — Dennis Heyer
(74) *Attorney, Agent, or Firm* — Crowell & Moring LLP

(57) ABSTRACT

Provided is an adhesive patch containing ropinirole serving as a therapeutic drug for Parkinson's disease, with the ropinirole used being free ropinirole (ropinirole in free form) added to an adhesive base, wherein the patch exhibits favorable drug permeability and excellent drug stability. Also provided is a transdermal absorption patch using, as an adhesive base, an acrylic-based adhesive having no specific carboxyl group and having a hydroxyl group or a pyrrolidone group, with the patch including free ropinirole added to the adhesive base. Further provided is a ropinirole-containing transdermal absorption patch including a transdermal absorption promoting agent.

14 Claims, 4 Drawing Sheets

ROPINIROLE-CONTAINING ADHESIVE PATCH

CROSS REFERENCE TO RELATED APPLICATIONS

This application is a continuation of U.S. application Ser. No. 14/362,001, filed May 30, 2014, which is a 371 of International Application No. PCT/JP2012/081083, the disclosures of which are expressly incorporated by reference herein.

TECHNICAL FIELD

The present invention relates to an adhesive patch that uses, as a main base, an acrylic-based adhesive having a hydroxyl group or a pyrrolidone group and having no carboxyl group and contains free form of ropinirole in the base.

BACKGROUND ART

Ropinirole was developed as a dopamine agonist and is used for treatment of Parkinson's disease, and oral preparations of ropinirole are distributed in the market. There have been attempts to formulate ropinirole into patches (Patent Documents 1 and 2).

One advantage of the patches is that the preparations can be easily removed when a side effect occurs.

At present, ropinirole distributed in the market is its acid addition salt (specifically, ropinirole hydrochloride) because of its stability and handleability, and it is contemplated that transdermal absorption preparations are produced using the acid addition salt of ropinirole (Patent Document 3). However, generally, a transdermal absorption preparation using a drug in the form of acid addition salt has a drawback in that transdermal absorbability is much lower than that when a free drug (drug in free form) is used. When a dehydrochlorinating agent is used to convert the acid addition salt of ropinirole to free ropinirole within the preparation, the amount of the drug contained in the adhesive base is limited, and the acid addition salt is not completely converted to free ropinirole, so that transdermal absorbability may not be increased so much. In addition, a metal salt may precipitate in the adhesive base, causing problems such as deterioration of the physical properties of the patch and skin irritation by the metal salt.

PRIOR ART LIST

Patent Document

Patent Document 1: Japanese Translation of PCT International Application No. 2001-518058
Patent Document 2: Japanese Translation of PCT International Application No. Hei 11-506462
Patent Document 3: International Publication WO2009/107478

DISCLOSURE OF INVENTION

Problem to be Solved by the Invention

In view of the foregoing problems, the present invention provides an adhesive patch containing free ropinirole (ropinirole in free form) in an adhesive base with the patch exhibiting favorable drug permeability and high drug stability.

Means for Solving the Problem

To solve the above problems, the present inventors have conducted extensive studies and confirmed that, when free ropinirole is added to a specific acrylic-based adhesive in consideration of the chemical characteristics of ropinirole, favorable drug permeability and high drug stability can be obtained. Thus, the present invention has been completed.

Accordingly, as a basic aspect the present invention is a transdermal absorption patch including: an acrylic-based adhesive serving as an adhesive base, having no carboxyl group and having a hydroxyl group or a pyrrolidone group; and free ropinirole added to the adhesive base.

As a specific aspect the present invention is a transdermal absorption patch including: an acrylic-based adhesive serving as an adhesive base, containing no cross-linking agent, having no carboxyl group, and having a hydroxyl group or a pyrrolidone group; and free ropinirole added to the adhesive base.

As another specific aspect the present invention is a transdermal absorption patch including: an acrylic-based adhesive serving as an adhesive base, containing no cross-linking agent, having no carboxyl group, and having a hydroxyl group or a pyrrolidone group; and free ropinirole added to the adhesive base; wherein the transdermal absorption patch further includes a transdermal absorption enhancer added thereto.

As a specific aspect, the present invention is the transdermal absorption patch wherein the acrylic-based adhesive is a 2-ethylhexyl acrylate/vinyl acetate/2-hydroxyethyl acrylate copolymer.

As another specific aspect, the present invention is the transdermal absorption patch wherein the acrylic-based adhesive is a 2-ethylhexyl acrylate/vinylpyrrolidone copolymer.

More specifically, the present invention is the transdermal absorption patch wherein the transdermal absorption enhancer is one or two or more kinds selected from triethyl citrate, glycerin, sorbitan monolaurate, oleyl alcohol, and isopropyl myristate.

More specifically, the present invention is the transdermal absorption patch wherein the transdermal absorption enhancer in the acrylic-based adhesive is one or two or more kinds selected from lauryl alcohol and isopropyl myristate.

Still another specific aspect of the present invention is a transdermal absorption patch including: an acrylic-based adhesive serving as an adhesive base, containing no cross-linking agent, having no carboxyl group, and having a hydroxyl group or a pyrrolidone group; and free ropinirole added to the adhesive base, wherein, when a crystal seeding method (CS method) is preformed, a factor (C) representing the growth degree of ropinirole crystals in the adhesive satisfies (C)≤1.

The CS method will be described later.

Effect of the Invention

According to the present invention, the transdermal absorption patch includes: an acrylic-based adhesive serving as an adhesive base, having no carboxyl group and having a hydroxyl group or a pyrrolidone group; and free ropinirole added to the adhesive base. By this configuration, the free ropinirole is completely dissolved in the acrylic adhesive serving as the adhesive base, so that the patch obtained can allow high transdermal absorbability and have excellent drug stability.

Therefore, with the transdermal absorption patch provided by the present invention, the free ropinirole serving as an active ingredient is transdermally absorbed from the adhesive layer in a favorable manner, so that the transdermal absorption patch is effective for treatment of Parkinson's disease.

MODES FOR CARRYING OUT THE INVENTION

Figure 1:
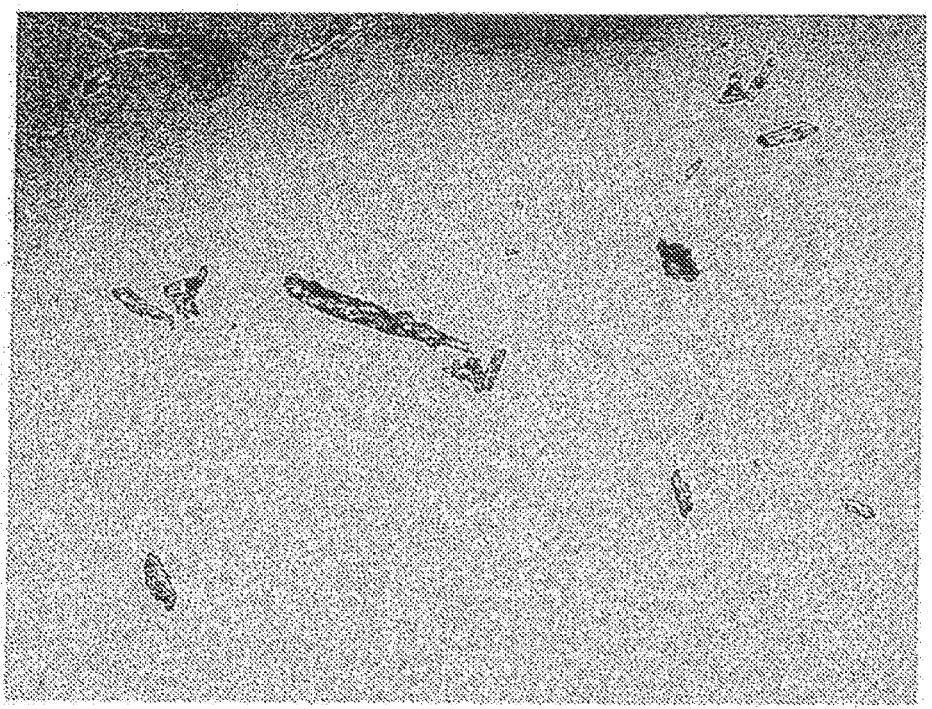
FIG. 1 is a micrograph showing the appearance of the surface of an adhesive base in Example 1 of the present invention during a CS method test immediately after the start of the test.
Figure 2:
FIG. 2 is a micrograph showing the appearance of the surface of the adhesive base in Example 1 of the present invention after completion of the CS method test.
Figure 3:
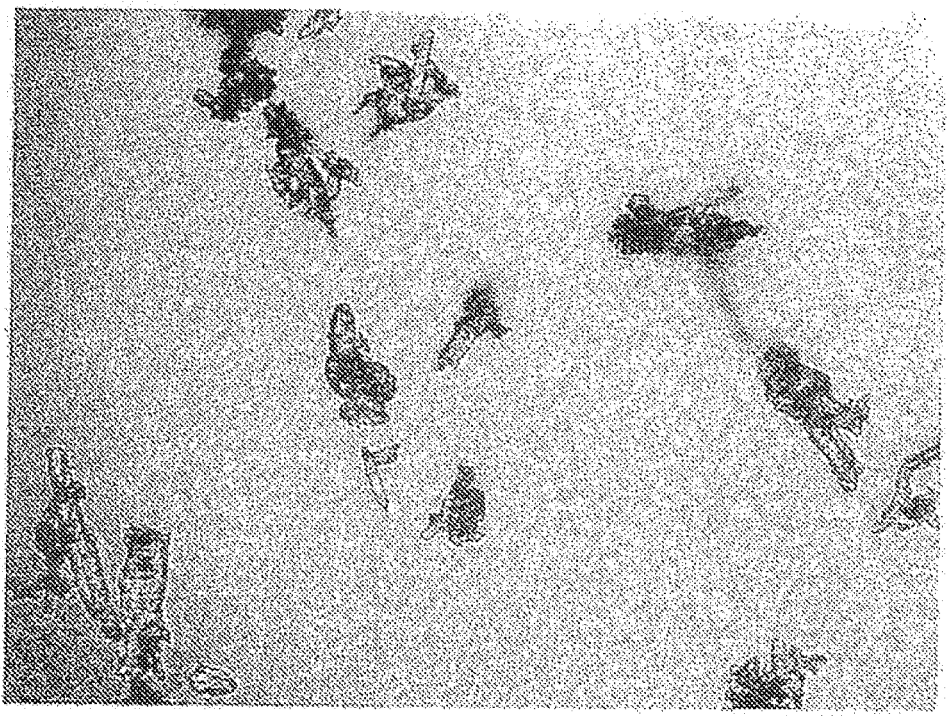
FIG. 3 is a micrograph showing the appearance of the surface of an adhesive base in Reference Example 2 during the CS method test immediately after the start of the test.
Figure 4:
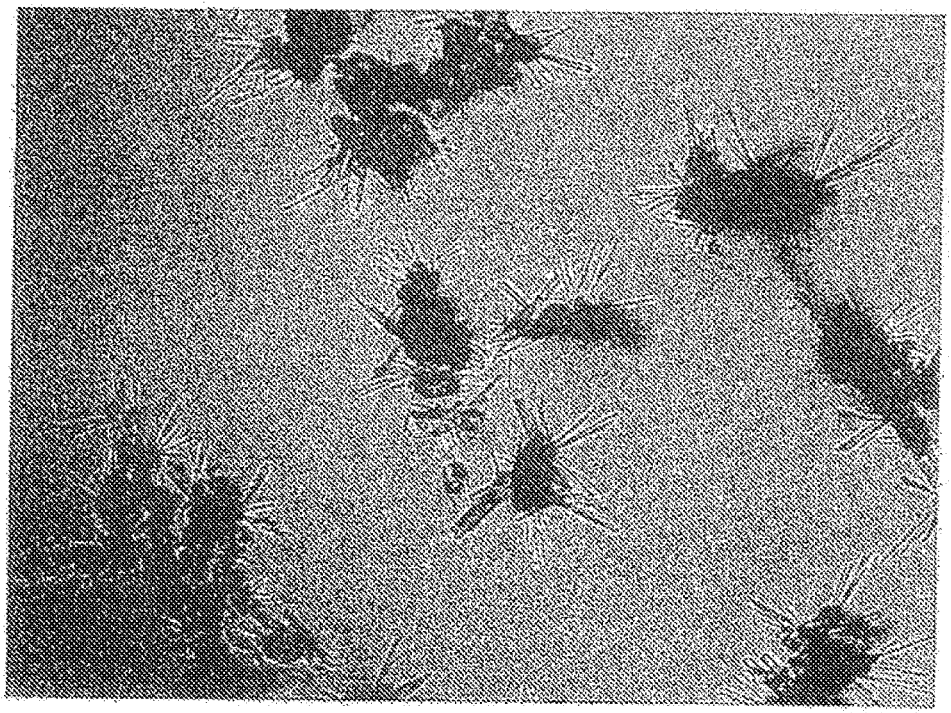
FIG. 4 is a micrograph showing the appearance of the surface of the adhesive base in Reference Example 2 after completion of the CS method test.

A basic aspect of the present invention is a transdermal absorption patch in which free ropinirole is added to a specific acrylic-based adhesive base.

No particular limitation is imposed on the amount of free ropinirole added to the transdermal absorption patch provided by the present invention, so long as the patch can be prepared. The amount of free ropinirole added is preferably within the range of 3 to 30% by weight, more preferably 7 to 20% by weight, and still more preferably 8 to 15% by weight based on the weight of the entire composition of the adhesive layer.

If the amount of free ropinirole added is less than 3% by weight, transdermal absorbability is insufficient. If the amount added is 30% by weight or more, the physical properties of the patch are impaired, and also such an amount is economically disadvantageous and is not preferred.

The acrylic-based adhesive serving as the main base of the transdermal absorption patch provided by the present invention is preferably an acrylic-based adhesive having a hydroxyl group or a pyrrolidone group and having no carboxyl group.

In the present invention, it is preferable that no cross-linking agent be added to the acrylic-based adhesive. The addition of a cross-linking agent tends to facilitate the decomposition reaction of ropinirole serving as the main active ingredient, to cause a reduction in the amount of the main active ingredient, and to facilitate generation of decomposition products. However, when the physical properties of the adhesive layer cannot be maintained unless a cross-linking agent is added, it is necessary to take measures for suppressing the reaction of the drug and the cross-linking agent.

In view of the above, it is preferable in the present invention that the acrylic-based adhesive used be an acrylic-based adhesive containing no cross-linking agent or an acrylic-based adhesive having enhanced cohesion with no cross-linking agent added thereto.

The acrylic-based adhesive having no carboxyl group and having a hydroxyl group is, for example, an acrylic-based adhesive famed from an alkyl (meth)acrylate having 1 to 18 carbon atoms and a monomer having a hydroxyl group. No particular limitation is imposed on the alkyl (meth)acrylate, and examples thereof may include alkyl (meth)acrylates such as butyl (meth)acrylate, isobutyl (meth)acrylate, octyl (meth)acrylate, 2-ethylhexyl (meth)acrylate, isooctyl (meth)acrylate, decyl (meth)acrylate, isodecyl (meth)acrylate, lauryl (meth)acrylate, stearyl (meth)acrylate, and ethyl (meth)acrylate. These may be used singly or in combination of two or more. Examples of the monomer having a hydroxyl group may include hydroxyalkyl (meth)acrylates such as 2-hydroxyethyl (meth)acrylate and hydroxypropyl (meth)acrylate.

As the acrylic-based adhesive having no carboxyl group and having a hydroxyl group, examples may include 2-ethylhexyl acrylate/vinyl acetate/2-hydroxyethyl acrylate/glycidyl methacrylate copolymer, and 2-ethylhexyl acrylate/vinyl acetate/2-hydroxyethyl acrylate copolymer. Specifically, for example, Duro-tak acrylic adhesives having a hydroxyl group and available from National Starch and Chemical Company (grades: Duro-tak 87-2510, Duro-tak 87-2516, Duro-tak 87-4287, Duro-tak 87-2287, etc.) can be preferably used. Of these, Duro-tak 87-4287, which is an adhesive that shows sufficiently high cohesion with no cross-linking agent added, is more preferable.

For example, an acrylic-based adhesive formed from an alkyl (meth)acrylate having 1 to 18 carbon atoms and a monomer having a pyrrolidone group is used as the acrylic-based adhesive used in the present invention that has no carboxyl group and has a pyrrolidone group. No particular limitation is imposed on the alkyl (meth)acrylate, and examples thereof may include alkyl (meth)acrylates such as butyl (meth)acrylate, isobutyl (meth) acrylate, octyl (meth)acrylate, 2-ethylhexyl (meth) acrylate, isooctyl (meth)acrylate, decyl (meth)acrylate, isodecyl (meth)acrylate, lauryl (meth)acrylate, stearyl (meth)acrylate, and ethyl (meth)acrylate. These may be used singly or in combination of two or more. Examples of the monomer having a pyrrolidone group and copolymerizable with the alkyl (meth)acrylate may include N-vinyl-2-pyrrolidone and methylvinylpyrrolidone. Preferred examples of the adhesive may include a 2-ethylhexyl acrylate/vinylpyrrolidone copolymer.

When an acrylic-based adhesive having no hydroxyl group and no pyrrolidone group is used, the high solubility of free ropinirole serving as the medicinal ingredient cannot be obtained.

When an acrylic-based adhesive having a carboxyl group is used, ropinirole serving as the main active ingredient is not released from the adhesive, so that high transdermal absorbability cannot be obtained.

In the transdermal absorption patch provided by the present invention, the average molecular weight (MW) of the acrylic-based adhesive used is preferably 300,000 or more and more preferably 400,000 or more.

The content of the acrylic-based adhesive used is preferably 30 to 98% by weight and more preferably 50 to 95% by weight based on the mass of the entire composition of the adhesive layer.

The transdermal absorption patch of the present invention may contain a transdermal absorption enhancer. Examples of the transdermal absorption enhancer may include methyl laurate, hexyl laurate, triethyl citrate, isopropyl myristate (hereinafter abbreviated as IPM), myristyl myristate, octyldodecyl myristate, cetyl palmitate, triacetin, cetyl lactate, lauryl lactate, methyl salicylate, glycol salicylate, ethylene glycol salicylate, diethyl sebacate, diisopropyl sebacate, medium-chain fatty acid triglyceride, lauryl alcohol, stearyl alcohol, isostearyl alcohol, myristyl alcohol, oleyl alcohol, cetanol, glycerin monocaprylate, glycerin monolaurate, glycerin monooleate, sorbitan monolaurate, sorbitan monooleate, sucrose monolaurate, polysorbate 20, propylene glycol monolaurate, polyethylene glycol monostearate, lauromacrogol, HCO-60, lauric acid diethanolamide, N-methyl-2-pyrrolidone, 1-ethyl-2-pyrrolidone, 5-methyl-2-pyrrolidone, N-octyl-2-pyrrolidone, dimethyl sulfoxide, glycerin, sorbitan monolaurate, and crotamiton.

Of these, one or two or more kinds selected from triethyl citrate, glycerin, oleyl alcohol, sorbitan monolaurate, and isopropyl myristate are preferably used, and one or two or more kinds selected from oleyl alcohol and isopropyl myristate are more preferred.

The amount added of the transdermal absorption enhancer is 0.1 to 20% by weight, preferably 0.1 to 10% by weight, and more preferably 2 to 10% by weight based on the weight of the entire composition of the adhesive layer. If the amount added of the absorption enhancer is less than 0.1 weight, the transdermal absorbability is not improved. On the other hand, if the amount added of the transdermal absorption enhancer is more than 20 weight, the physical properties of the preparation deteriorate.

Preferably, the transdermal absorption patch provided by the present invention contains an antioxidant. Preferred examples of the antioxidant may include BHT (butylhydroxytoluene), concentrated mixed tocopherol, tocopherol, tocopherol acetate, 2-mercaptobenzimidazole, pentaerythrityl-tetrakis, and ascorbic acid. Of these, BHT and tocopherol are particularly preferred.

The amount added of the antioxidant is 0.1 to 5% by weight and preferably 0.1 to 2% by weight based on the mass of the entire composition of the adhesive layer.

If necessary, the transdermal absorption patch provided by the present invention may contain liquid components such as a softening agent and a resolvent.

Examples of the softening agent may include polyisobutylene, polybutene, lanolin, castor oil, almond oil, olive oil, camellia oil, persic oil, peanut oil, process oil, extender oil, and liquid paraffin.

Examples of the resolvent may include: fatty acid esters such as isopropyl myristate, diethyl sebacate, diisopropyl sebacate, diisopropyl adipate, and isopropyl palmitate; and polyols such as propylene glycol, polyethylene glycol, butylene glycol, and glycerin.

Moreover, various base components used in ordinary external preparations can be used for the transdermal absorption patch of the present invention, so long as the base components have no influence on the other components.

No particular limitation is imposed on these base components, and examples thereof may include: water-soluble polymers such as polyvinylpyrrolidone, polyvinyl alcohol, and polyacrylic acid; cellulose derivatives such as ethyl cellulose, hydroxypropyl cellulose, and hydroxypropyl methyl cellulose; silicon compounds such as silicic acid anhydride and light silicic acid anhydride; and inorganic fillers such as zinc oxide, aluminum oxide, titanium dioxide, silica, magnesium oxide, iron oxide, and stearic acid.

Moreover, a preservative, an algefacient, an antimicrobial, a flavoring agent, a colorant, etc. may be added as needed.

No particular limitation is imposed on the support for the transdermal absorption patch provided by the present invention, and any of stretchable and non-stretchable supports may be used.

More specifically, the support used may be any of paper materials and films, sheets, stacks thereof, porous membranes, foamed materials, woven fabrics, and nonwoven fabrics formed from synthetic resins such as polyethylene terephthalate, polyethylene, polypropylene, polybutadiene, ethylene-vinyl acetate copolymers, polyvinyl chloride, polyester, nylon, and polyurethane.

A release liner formed of, for example, polyethylene terephthalate, polypropylene, or paper may be used, and polyethylene terephthalate is particularly preferred.

If necessary, the release liner may be subjected to silicon treatment to obtain optimal peel force.

A deoxidizer may be allowed to coexist with the transdermal absorption patch of the present invention. The deoxidizer used is preferably a deoxidizer famed from iron as a raw material or a deoxidizer formed from a nonferrous metal as a raw material. Examples of the method of allowing the deoxidizer to coexist include a method in which the deoxidizer is directly sealed in a package bag and a method in which a package bag formed from a stack including a deoxidizer film is used.

In the transdermal absorption patch of the present invention, the stability of ropinirole in the adhesive base can be relatively easily checked using a crystal seeding method (CS method), which is a simple method of testing stability of a drug. The CS method is a test method in which crystals of a drug are scattered on an adhesive base and the growth degree of the crystals of the drug is observed to determine the short-term stability of the drug in the adhesive base.

For the patch of the present invention, the long-term stability of the drug in the preparation can be estimated from the results of the CS method. Specifically, when dissolution of the scattered drug into the adhesive base is found in the results of the CS method or the growth of the crystals of the scattered drug is not observed in the results, it can be judged that the possibility of crystallization of the drug even under long-term storage conditions is low. When the growth of the crystals of the drug is observed in the CS method, it is feared that crystals of the drug may precipitate in the preparation under long-term storage conditions.

More specifically, the CS method is performed in the following manner, and the stability of the crystals of the drug in the preparation is evaluated according to the evaluation criteria described later.

<Test Procedure of CS Method>

A release film of a patch is removed. Then a support of the patch is secured to a glass slide, and this patch is used as a test specimen. Alternatively, part of the adhesive in the patch is collected, and the collected adhesive is applied to a glass slide and used as a test specimen.

Next, bulk powder of ropinirole is scattered directly on the adhesive portion of the test specimen. No particular limitation is imposed on the particle diameter of the scattered drug, but the particle diameter of the drug used is preferably 0.1 to 5,000 µm, in order to clearly observe the generation of crystals of the scattered drug.

The crystals of the drug immediately after they are scattered are observed under an electron microscope (for example, a digital microscope VHX-600 manufactured by KEYENCE), and image data inputted from the electron microscope through an image data processing unit is outputted.

Then DSB/S, i.e., the ratio of the total area of the crystals of the scattered drug (the projected area from above: DSB) per unit area (S) of the adhesive, is determined on the basis of the outputted image data.

After the test specimen is left to stand at room temperature for 3 to 10 days, the test specimen is observed under the electron microscope in the same manner as immediately after the crystals are scattered. Then DSA/S, i.e., the ratio of the total area of the crystals of the scattered drug (the projected area from above: DSA) per unit area (S) of the adhesive, is similarly determined.

A factor (C) representing the growth degree of the crystals of the scattered drug in each test specimen is determined from the obtained values of DSB/S and DSA/S as follows.

$$(C)=(b)/(a)$$

[In the formula above, (a): the ratio of the total area of the crystals of the scattered drug (the projected area from above: DSB) scattered in a certain area (S) on the surface of the adhesive, i.e., DSB/S, immediately after the start of the test (immediately after the crystals of the drug are scattered).

(b): the ratio of the total area of the crystals of the scattered drug (the projected area from above: DSA) scattered in the certain area (S) on the surface of the adhesive, i.e., DSA/S, after completion of the test (10 days after the crystals of the drug are scattered).]

<Evaluation Criteria>

Evaluation is made using the value of (C) obtained above according to the evaluation criteria below.

$$(C) \leq 1: \qquad (i)$$

Growth of the crystals of the drug scattered on the adhesive is not observed, or the crystals are reduced in size.

$$(C) \geq 1: \qquad (ii)$$

The crystals of the drug scattered on the adhesive have grown.

An example of a method of producing the transdermal absorption patch provided by the present invention will next be described.

Specifically, the acrylic-based adhesive, free ropinirole, and other components such as an antioxidant are dissolved in a suitable solvent using a mixer to obtain an adhesive solution. The solvent used may be ethyl acetate, ethanol, methanol, etc. A suitable solvent is selected according to the components, and only one solvent or a combination of two or more solvents may be used.

Next, the thus-obtained adhesive solution is spread over a release film or a support, and the solvent is removed by drying. Then the support and the release film are laminated with each other, whereby a transdermal absorption patch can be obtained.

The thickness of the adhesive layer is preferably about 30 to about 200 μm and more preferably about 50 to about 100 μm.

If the thickness is less than 30 μm, the duration of release of the drug becomes short. If the thickness is larger than 200 μm, the amount of the drug contained in the adhesive layer becomes large, and this causes an increase in production cost.

EXAMPLES

The present invention will next be more specifically described by way of Examples and Comparative Examples, but the present invention is not limited to the following Examples.

Example 1

Ethyl acetate was used as a solvent, and free ropinirole and an acrylic-based adhesive (2-ethylhexyl acrylate/vinyl acetate/2-hydroxyethyl acrylate copolymer; product name: Duro-tak 87-4287) were mixed using a mixer to obtain an adhesive solution.

The adhesive solution was spread over a release-treated film, and the solvent was removed by drying to form an adhesive layer having a thickness of 60 to 70 μm. Then a support was placed on the adhesive layer to press-bond and transferred the adhesive layer, whereby a patch was obtained.

The amounts added of the respective components (unit: % by weight) and the mixing ratio are shown in TABLE 1.

Examples 2 to 5

Respective patches in Examples 2 to 5 having compositions shown in TABLE 1 (unit: % by weight) were obtained in accordance with the production method in Example 1.

Reference Examples 1 and 2

Patches in Reference Examples 1 and 2 having compositions shown in TABLE 1 (unit: % by weight) were obtained in accordance with the production method in Example 1.

TABLE 1

|  | Examples | | | | | Ref. Examp. | |
| --- | --- | --- | --- | --- | --- | --- | --- |
|  | 1 | 2 | 3 | 4 | 5 | 1 | 2 |
| Free form of Ropinirole | 10 | 8 | 8 | 5 | 10 | 5 | 12 |
| BHT | — | 1 | — | — | — | — | — |
| Duro-tak 87-4287 [1] | 90 | 91 | 92 | 95 | — | — | 88 |
| Ethylhexyl acrylate/vinylpyrrolidone copolymer [2] | — | — | — | — | 90 | — | — |
| Duro-tak 87-2516 [3] | — | — | — | — | — | 95 | — |

Note
[1] Duro-tak 87-4287: 2-ethylhexyl acrylate/vinyl acetate/2-hydroxyethyl acrylate copolymer (an acrylic-based adhesive containing no cross-linking agent, having a hydroxyl group, and having no carboxyl group)

Note
[2] Ethylhexyl acrylate/vinylpyrrolidone copolymer: an acrylic-based adhesive containing no cross-linking agent, having a pyrrolidone group, and having no carboxyl group Note
[3] Duro-tak 87-2516: an acrylic-based adhesive containing a cross-linking agent, having a hydroxyl group, and having no carboxyl group Examples 6 to 13

Patches in Examples 6 to 13 having compositions shown in TABLE 2 (unit: % by weight) were obtained in accordance with the production method in Example 1.

TABLE 2

|  | Examples | | | | | | | |
|---|---|---|---|---|---|---|---|---|
|  | 6 | 7 | 8 | 9 | 10 | 11 | 12 | 13 |
| Free form of Ropinirole | 10 | 10 | 10 | 10 | 10 | 12 | 14 | 12 |
| Duro-tak 87-4287 [1] | 85 | 85 | 88 | 85 | 85 | 83 | 81 | 83 |
| Triethyl citrate | 5 | — | — | — | — | — | — | — |
| Glycerin | — | 5 | — | — | — | — | — | — |
| Sorbitan monolaurate | — | — | 2 | — | — | — | — | — |
| Oleyl alcohol | — | — | — | 5 | — | 5 | 5 | — |
| Isopropyl myristate | — | — | — | — | 5 | — | — | 5 |

Note
[1] Duro-tak 87-4287: 2-ethylhexyl acrylate/vinyl acetate/2-hydroxyethyl acrylate copolymer (an acrylic-based adhesive containing no cross-linking agent, having a hydroxyl group, and having no carboxyl group)

Comparative Examples 1 and 2

Patches in respective Comparative Examples were produced in the same manner as in Example 1 except that respective components were used in ratios shown in TABLE 3 (unit: % by weight).

Comparative Example 3

With reference to a prescription and a production method in Example 3 in International Publication WO2009/107478, a patch in Comparative Example 3 was produced. The prescription (unit: % by weight) is shown in TABLE 3.

TABLE 3

|  | Comparative Examples | | |
|---|---|---|---|
|  | 1 | 2 | 3 |
| Free form of Ropinirole | 10 | 10 | — |
| Ropinirole hydrochloride | — | — | 5 |
| Sodium hydroxide | — | — | 0.5 |
| 2-Ethylhexyl acrylate/dodecyl methacrylate copolymer [4] | 90 | — | — |
| Duro-tak 87-2194 [5] | — | 90 | — |
| Duro-tak 87-900A [6] | — | — | 95 |

Note
[4] An acrylic-based adhesive containing no functional groups
Note
[5] Duro-tak 87-2194: an acrylic-based adhesive having a carboxyl group
Note
[6] Duro-tak 87-900A: an acrylic-based adhesive having no hydroxyl group and no carboxyl group Test Example 1: Examination of Stability of Drug in Preparations by Crystal Seeding Method (CS Method)

The stability of the drug in each of the preparations in Examples 1 to 13, Reference Examples 1 and 2, and Comparative Examples 1 and 2 was examined by the CS method. The test procedure and the evaluation criteria for the test results are shown below, and the test results are shown in TABLE 4 and 5.

The test procedure of the CS method was the same as that described above for the CS method.

The adhesive portion in each of the Examples and Comparative Examples was collected as a test sample, and the test sample was applied to a glass slide and used as a test specimen.

Observation by a microscope was performed using a digital microscope (type: KEYENCE VHX-600, magnification: 400×). The particle diameter of the used raw ropinirole scattered on the adhesive was 5 to 3,000 μm, and the test was terminated 10 days after the drug was scattered.

In each TABLE, the factor (C) representing the degree of growth of crystals is shown as circle or cross according to the following evaluation criteria.

◯: when (C)<1
x: when (C)>1

As can be seen from the results of the above test, in the adhesives in Examples 1 to 13 that are used as the transdermal absorption patches of the present invention, growth of the crystals was not observed, and it was found that ropinirole was stably dissolved in the adhesive base. However, in the preparations in Comparative Example 1 and Reference Example 2, growth of the crystals was found after completion of the test, and it was suggested that ropinirole was present in the adhesive base in an unstable state.

TABLE 4

|  | Examples | | | | | Reference Examples | | Comparative Examples | |
|---|---|---|---|---|---|---|---|---|---|
|  | 1 | 2 | 3 | 4 | 5 | 1 | 2 | 1 | 2 |
| Growth of Crystals | ◯ | ◯ | ◯ | ◯ | ◯ | ◯ | X | X | ◯ |

TABLE 5

|  | Examples | | | | | | | |
|---|---|---|---|---|---|---|---|---|
|  | 6 | 7 | 8 | 9 | 10 | 11 | 12 | 13 |
| Growth of Crystals | ◯ | ◯ | ◯ | ◯ | ◯ | ◯ | ◯ | ◯ |

Test Example 2: Examination of Recrystallization of Drug in Preparations Store for Long Time Each of the patches obtained in the above Examples and Comparative Examples was cut into a size of 2.5×2.5 cm, and the cut pieces were individually packaged in package bags having a polyacrylonitrile innermost layer and stored at room temperature for 6 months. Then, for each stored specimen, the package bag was opened, and whether or not free ropinirole were crystallized in the adhesive was checked visually.

The results are shown in TABLE 6.

TABLE 6

|  | Examples | | | | | Reference Examples | | Comparative Examples | |
|---|---|---|---|---|---|---|---|---|---|
|  | 1 | 2 | 3 | 4 | 5 | 1 | 2 | 1 | 2 |
| Growth of Crystals | No | No | No | No | No | No | Yes | Yes | No |

For the adhesives in Examples 1 to 5 that are used as the transdermal absorption patches of the present invention, no crystallization of drug was found. The ropinirole was sufficiently dissolved in the adhesive, and it was found that the patches using these adhesives were preparations of the complete dissolution type.

The results of this test agree with the results of the test for examining the short-team stability in the patches by the CS method in Test Example 1.

Test Example 3: Stability Test for Principal Agent

The patches in Example 4 and Reference Example 1 that had been stored under the storage condition of 40° C. for one month were punched into a size of 6.25 cm$^2$ and placed in 50 mL centrifugal precipitation tubes. Tetrahydrofuran (hereinafter abbreviated as THF) was added to each tube, and ultrasonic extraction and extraction using a shaker were performed. The obtained extract was collected in a 100-mL volumetric flask, and the volume was adjusted to 100 mL with THF.

6 mL of the extract was collected, and its volume was adjusted to 50 mL using a 15% acetonitrile aqueous solution. Then the resultant solution was filtrated through a membrane filter (0.45 μm), and the content of ropinirole was measured by HPLC.

The HPLC measurement conditions are as follows.
Column: waters spherisorb 3CN (3×150 mm)
Mobile phase: acetonitrile:water:phosphoric acid=150:850:0.85
Flow rate: 0.4 mL/min
Wavelength: 249 nm
Injection amount: 10 μL
The results are shown in TABLE 7.
The results are represented as relative values (%) with respect to the initial amounts of ropinirole.

TABLE 7

| Test Patch | Example 4 | Reference Example 1 |
| --- | --- | --- |
| Relative values (%) to initial value | 97.4 | 94.2 |

As can be seen from the results in TABLE 7, it was found that the transdermal absorption patch of the present invention is a preparation with excellent stability of free ropinirole serving as the principal agent.

Test Example 4: Skin Permeation Test on Hairless Mice

The patches in Example 1, Examples 4 to 13, and Comparative Examples 2 and 3 were subjected to an in vitro skin permeation test using skin excised from hairless mice (HR-1, 7 week old).

The back skin of a hairless mouse was removed. The dermis was set on a receptor with its inside filled with phosphate buffered saline, and warm water at 37° C. was refluxed through a water jacket.

Each test patch was punched into a circular shape (1.54 cm$^2$) and applied to the excised skin. The receptor solution was sampled at time intervals, and the skin permeation amount of the drug was measured by the high-performance liquid chromatography. The rate of transdermal absorption (Flux: μg/cm$^2$/hr) in steady state was computed from the results of the measurement.

The test was performed for each of five combinations of test specimens [Test Examples 4-(1) to (5)] shown in TABLES 8 to 12.

The results are shown in TABLES 8 to 12. In TABLES 8 to 10, the results are shown by the rate of transdermal absorption and the relative rate of transdermal absorption. In TABLES 11 and 12, the results are shown only by the relative ratio of transdermal absorption.

Figure 5:
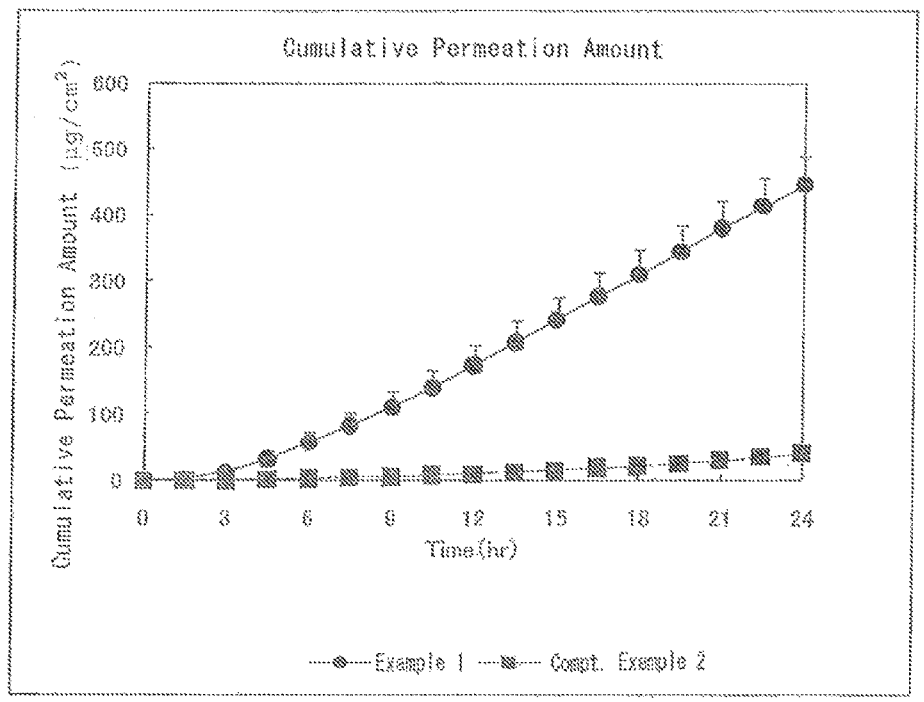
FIG. 5 is a view showing the results of a skin permeation test in Test Example 4-(1) of the present invention.
Figure 6:
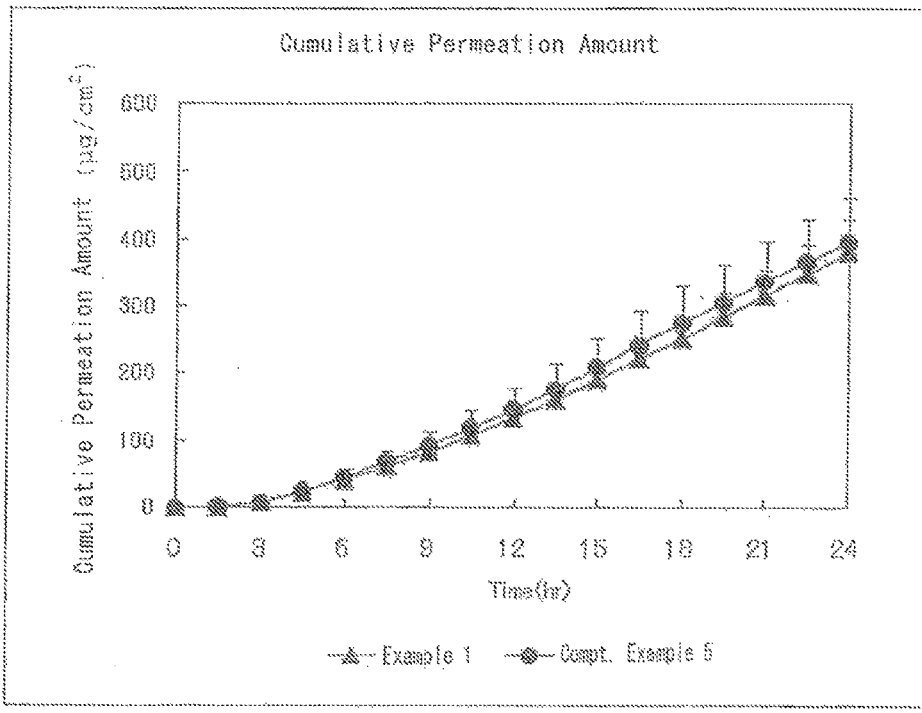
FIG. 6 is a view showing the results of the skin permeation test in Test Example 4-(2) of the present invention.
Figure 7:
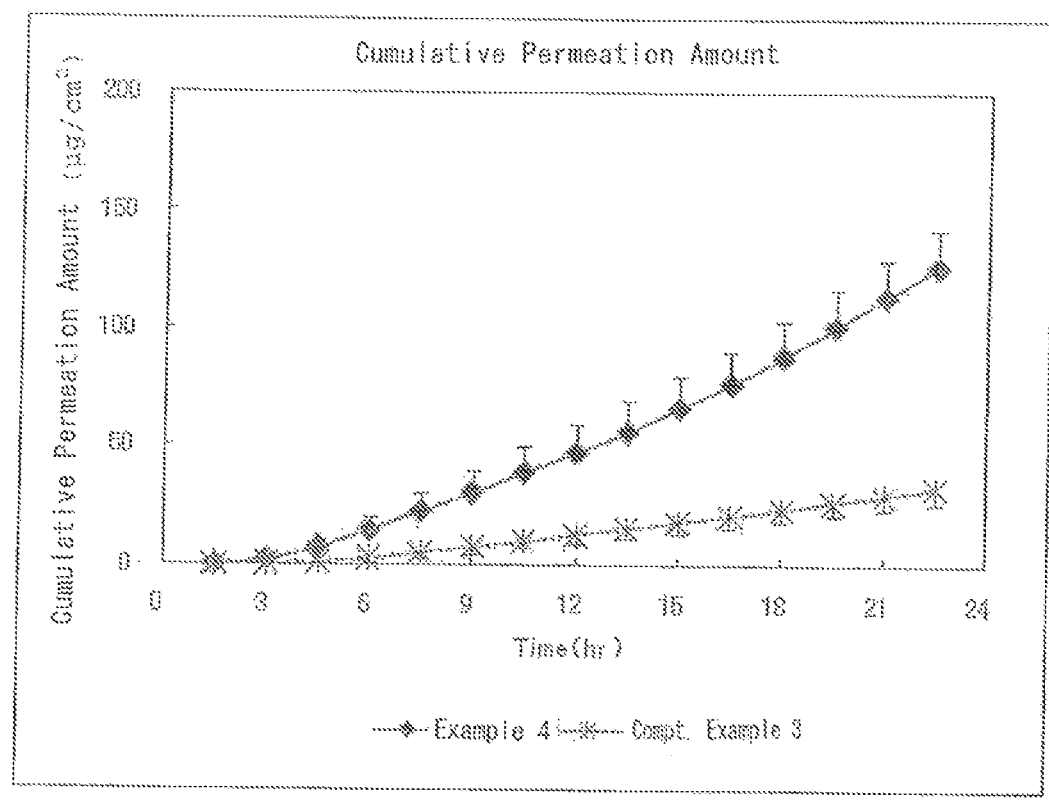
FIG. 7 is a view showing the results of the skin permeation test in Test Example 4-(3) of the present invention.

The results for Test Examples 4-(1), 4-(2), and 4-(3) are also shown in FIGS. 5 to 7.

In FIGS. 5 to 7, the results are shown as the cumulative permeation amount.

TABLE 8

| Test Example 4-(1) | | |
| --- | --- | --- |
| Test Patch | Rate of Transdermal Absorption (Flux: μg/cm$^2$/hr) | Relative Rate of Transdermal Absorption (vs. Example 1) |
| Example 1 | 22.56 | 1.00 |
| Compt. Example 2 | 2.44 | 0.11 |

TABLE 9

| Test Example 4-(2) | | |
| --- | --- | --- |
| Test Patch | Rate of Transdermal Absorption (Flux: μg/cm$^2$/hr) | Relative Rate of Transdermal Absorption (vs. Example 1) |
| Example 1 | 20.58 | 1.00 |
| Example 5 | 22.81 | 1.01 |

TABLE 10

| Test Example 4-(3) | | |
| --- | --- | --- |
| Test Patch | Rate of Transdermal Absorption (Flux: μg/cm$^2$/hr) | Relative Rate of Transdermal Absorption (vs. Example 1) |
| Example 4 | 7.08 | 1.00 |
| Compt. Example 3 | 1.87 | 0.26 |

TABLE 11

| Test Patch | Relative Rate of Transdermal Absorption (vs. Example 1) |
| --- | --- |
| Example 1 | 1.00 |
| Example 6 | 1.10 |
| Example 7 | 1.45 |
| Example 8 | 1.39 |
| Example 9 | 1.68 |
| Example 10 | 1.68 |

TABLE 12

| Test Patch | Relative Rate of Transdermal Absorption (vs. Example 3) |
| --- | --- |
| Example 3 | 1.00 |
| Example 11 | 1.78 |
| Example 12 | 2.09 |
| Example 13 | 1.40 |

As can be seen from the results shown in the figures, the transdermal absorption patches of the present invention (Examples 1 and 4 to 13) are found to be preparations allowing much higher transdermal absorbability as compared to those in the transdermal absorption patches in Comparative Examples 2 and 3.

As can be seen from the test results in Test Examples 4-(3) and 4-(4), the preparations in Examples 6 to 13 each containing a transdermal absorption enhancer exhibited higher transdermal absorbability than those in Examples 1 and 3 each containing no transdermal absorption promoting agent.

INDUSTRIAL APPLICABILITY

As described above, the present invention can provide a transdermal absorption preparation containing free ropinirole and having favorable drug permeability and high drug stability and contributes significantly to the treatment of Parkinson's disease.

The invention claimed is:

1. A transdermal absorption patch comprising: an acrylic-based adhesive serving as an adhesive base, containing no cross-linking agent, having no carboxyl group, and having a hydroxyl group or a pyrrolidone group; and free ropinirole added to the acrylic-based adhesive.

2. A transdermal absorption patch comprising: an adhesive base comprising an acrylic-based adhesive containing no cross-linking agent, having no carboxyl group, and having a hydroxyl group or a pyrrolidone group; and free ropinirole added to the adhesive base, the transdermal absorption patch further comprising a transdermal absorption promoting agent added to the adhesive base.

3. The transdermal absorption patch according to claim 1, wherein the acrylic-based adhesive is a 2-ethylhexyl acrylate/vinyl acetate/2-hydroxyethyl acrylate copolymer.

4. The transdermal absorption patch according to claim 1, wherein the acrylic-based adhesive is a 2-ethylhexyl acrylate/vinylpyrrolidone copolymer.

5. The transdermal absorption patch according to claim 2, wherein the transdermal absorption enhancer is one or two or more kinds selected from triethyl citrate, glycerin, sorbitan monolaurate, oleyl alcohol, and isopropyl myristate.

6. The transdermal absorption patch according to claim 2, wherein the transdermal absorption enhancer is one or two or more kinds selected from oleyl alcohol and isopropyl myristate.

7. A transdermal absorption patch comprising: an acrylic-based adhesive serving as an adhesive base, containing no cross-linking agent, having no carboxyl group, and having a hydroxyl group or a pyrrolidone group; and free ropinirole added to the acrylic-based adhesive, when a crystal seeding method (CS method) is performed, a factor (C) representing a growth degree of ropinirole crystals in the adhesive satisfies $(C) \leq 1$, $$(C)=(b)/(a)$$

wherein,
(a): a ratio of a total area of crystals of a scattered drug (a projected area from above: DSB) scattered in a certain area (S) on a surface of the adhesive, i.e., DSB/S, immediately after the start of a test (immediately after the crystals of the drug are scattered), and
(b): a ratio of a total area of the crystals of the scattered drug (the projected area from above: DSA) scattered in the certain area (S) on the surface of the adhesive, i.e., DSA/S, after completion of the test (10 days after the crystals of the drug are scattered).

8. The transdermal absorption patch according to claim 2, wherein the acrylic-based adhesive is a 2-ethylhexyl acrylate/vinyl acetate/2-hydroxyethyl acrylate copolymer.

9. The transdermal absorption patch according to claim 2, wherein the acrylic-based adhesive is a 2-ethylhexyl acrylate/vinylpyrrolidone copolymer.

10. The transdermal absorption patch according to claim 3, wherein the transdermal absorption enhancer is one or two or more kinds selected from triethyl citrate, glycerin, sorbitan monolaurate, oleyl alcohol, and isopropyl myristate.

11. The transdermal absorption patch according to claim 4, wherein the transdermal absorption enhancer is one or two or more kinds selected from triethyl citrate, glycerin, sorbitan monolaurate, oleyl alcohol, and isopropyl myristate.

12. The transdermal absorption patch according to claim 3, wherein the transdermal absorption enhancer is one or two or more kinds selected from oleyl alcohol and isopropyl myristate.

13. The transdermal absorption patch according to claim 4, wherein the transdermal absorption enhancer is one or two or more kinds selected from oleyl alcohol and isopropyl myristate.

14. The transdermal absorption patch according to claim 5, wherein the transdermal absorption enhancer is one or two or more kinds selected from oleyl alcohol and isopropyl myristate.

* * * * *